United States Patent [19]

Hill, Jr.

[11] Patent Number: 4,802,762
[45] Date of Patent: Feb. 7, 1989

[54] OPTICAL INSPECTION OF POLYMER-BASED MATERIALS

[75] Inventor: Ralph H. Hill, Jr., San Antonio, Tex.

[73] Assignee: Southwest Research Institute, San Antonio, Tex.

[21] Appl. No.: 917,959

[22] Filed: Oct. 14, 1986

[51] Int. Cl.[4] .......................... G01J 3/30; G01N 21/64
[52] U.S. Cl. ..................................... 356/318; 356/417; 250/459.1
[58] Field of Search .................. 250/458.1, 459.1, 372, 250/503.1, 504 R; 356/318, 417

[56] References Cited

U.S. PATENT DOCUMENTS 4,018,530  4/1977  Hirschfeld .................. 250/459.1
4,580,059  4/1986  Wolfbeis .................... 250/458.1
4,642,526  2/1987  Hopkins ..................... 250/504 R
4,645,918  2/1987  Tsuchiya et al. ............ 356/318

Primary Examiner—Vincent P. McGraw
Assistant Examiner—William L. Oen
Attorney, Agent, or Firm—Hamilton, Smith & Clarkson

[57] ABSTRACT

An optical inspection system for using laser-induced luminescence to detect deterioration of a polymer-based material. The inspection system comprises an excitation means for illuminating a specimen of the polymer material to cause it to produce fluorescent radiation. The spectral representation of the fluorescence produced by the specimen is compared to the spectrum of a reference sample of known quality in order to obtain an indication of the physical characteristics of the specimen.

11 Claims, 4 Drawing Sheets

OPTICAL INSPECTION OF POLYMER-BASED MATERIALS

FIELD OF THE INVENTION

The present invention relates generally to the field of optical inspection of materials. More specifically, the present invention provides a method and apparatus for utilizing laser-induced fluorescence techniques to detect deterioration of a polymer material which might not be detectable using normal visual techniques.

BACKGROUND

Polyurethanes have found widespread use in recent years as liners for fuel tanks and other liquid chemical containers. These polymer materials provide effective, economical liquid barriers which are essential in maintaining the integrity of storage tanks. Over time, however, environmental factors, such as heat, ultraviolet light, or radiation exposure can cause degradation of the polyurethane material and, thus, a breach of the containment barrier.

Polymer degradation is often accompanied by a minor change in the material's color, as well as changes in many of its other physical characteristics. In cases of extreme degradation, the color change may be significant enough to be detected by visual inspection of the material. However, potentially dangerous degradation may occur long before the material exhibits a significant change in its visual characteristics. Moreover, certain materials, such as black polyurethane, may undergo shifts in color which are very difficult to detect by visual inspection or standard color measurement techniques.

For the reasons discussed above, it is apparent that there is a need for an effective inspection system for detecting the degradation of polymer-based materials which might not be apparent from a visual inspection of the material. The present invention overcomes the difficulties caused by standard color comparison techniques by providing an optical inspection system employing laser-induced fluorescence, as is discussed in greater detail below.

In order to understand the principles of operation of the present invention, it is important to understand the meaning of luminescence, as well as the historical evolution of the definition of luminescence. Historically, materials were said to exhibit characteristics of "luminescence" if they emitted photons after being irradiated with light having a wavelength in the range of approximately 1800 to 3700 Angstroms (ultraviolet). Prior art definitions of this phenomenon have included two categories: fluorescence and phosphorescence. A material was said to exhibit fluorescence if the luminescence ceased after termination of the irradiation. However, if the luminescence persisted after irradiation, the phenomena was termed phosphorescence.

The above-mentioned definitions evolved at a time when observations of the persistence of luminescence were made with the unaided eye. The development of sophisticated instruments capable of measuring the persistance of luminescence for very short time periods, e.g., nanoseconds, has led to a more precise definition of the above-mentioned terms and has changed the definition of luminescence for some materials. For example, it is now known that many materials which have been characterized in the literature as being fluorescent emit luminesence for as long as 1000 microseconds after termination of excitation. This luminescence offers significant information regarding the physical characteristics of the illuminated material and in the present invention can be used to detect deterioration of the material, as will be discussed in greater detail below.

It is well known that certain materials luminesce in the presence of ultraviolet or blue light and that the variation of the visible light luminescence can be used to determine certain features of the material. An example of an apparatus for using these phenomena to detect the presence of caries in human teeth is shown in U.S. Pat. Nos. 4,290,433 and 4,479,499 issued to Alfano. The luminescence in human teeth which is essential to the methods shown in these patents is dependent on the recognition of total visible luminescence. Further, the detection of the caries as shown therein relies on a visual recognition of differences in the color of the reradiated light from the teeth. While this luminescence technique is useful for detecting certain types of characteristics of materials, it is not suitable for an application such as that shown in the present invention because the technique is dependent on visual recognition of color differences in the luminescence of the material.

The invention method overcomes the shortcomings of previous optical inspection systems because it takes advantage of complex excitation-luminescence spectra of polyurethanes. Thus, two samples which both reflect approximately the same spectrum can have different fluorescence charactersitics which can be differentiated to distinguish between various grades of the material.

SUMMARY OF THE INVENTION

The present invention provides a method and apparatus for inspection and quality detection of a polymer material, based on fluorescence characteristics of the material at various stages of deterioration. Secifically, fluorescence from a new specimen of the polymer has a characteristic spectrum which can be compared to and differentiated from an aged or deteriorated sample of the material. Through the use of laser-induced luminescence, or more particularly laser-induced fluorescence, it is possible to detect minor differences in the characteristics of the polymer material which might not be detected using standard detection techniques, such as visual inspection or color comparison.

The invention system comprises an excitation source which illuminates a specimen of polymer material in order to cause that material to produce fluorscent radiation. In the preferred embodiment of the invention, the excitation source is a laser. A light detection means is operable to detect the fluorescent light produced by the material under examination and is operable to produce a spectral representation of that fluorescent light. The spectral representation is processed in a signal processing means capable of differentiating between the spectrum (or a portion of the spectrum) of new polymer material and that of aged material. An initial measurement of the fluorescent characteristics of a reference sample of the polymer material is made using the above-mentioned system. The spectral response produced by the reference material is analyzed by the invention system and is stored in memory for subsequent comparison with spectral responses of specimens of the polymer material.

The method of detecting deterioration of the polyurethane materials comprises the steps of illuminating the material with light from an excitation source, thereby causing the material to fluoresce; detecting the fluorescent light reradiated by the material and producing an output data signal in response thereto; processing the output data signal to obtain a spectral representation of the reradiated light; and comparing the spectrum of the material under examination to the spectrum of a reference sample of material.

DETAILED DESCRIPTION OF THE PREFERRED EMBODIMENT

Figure 1:
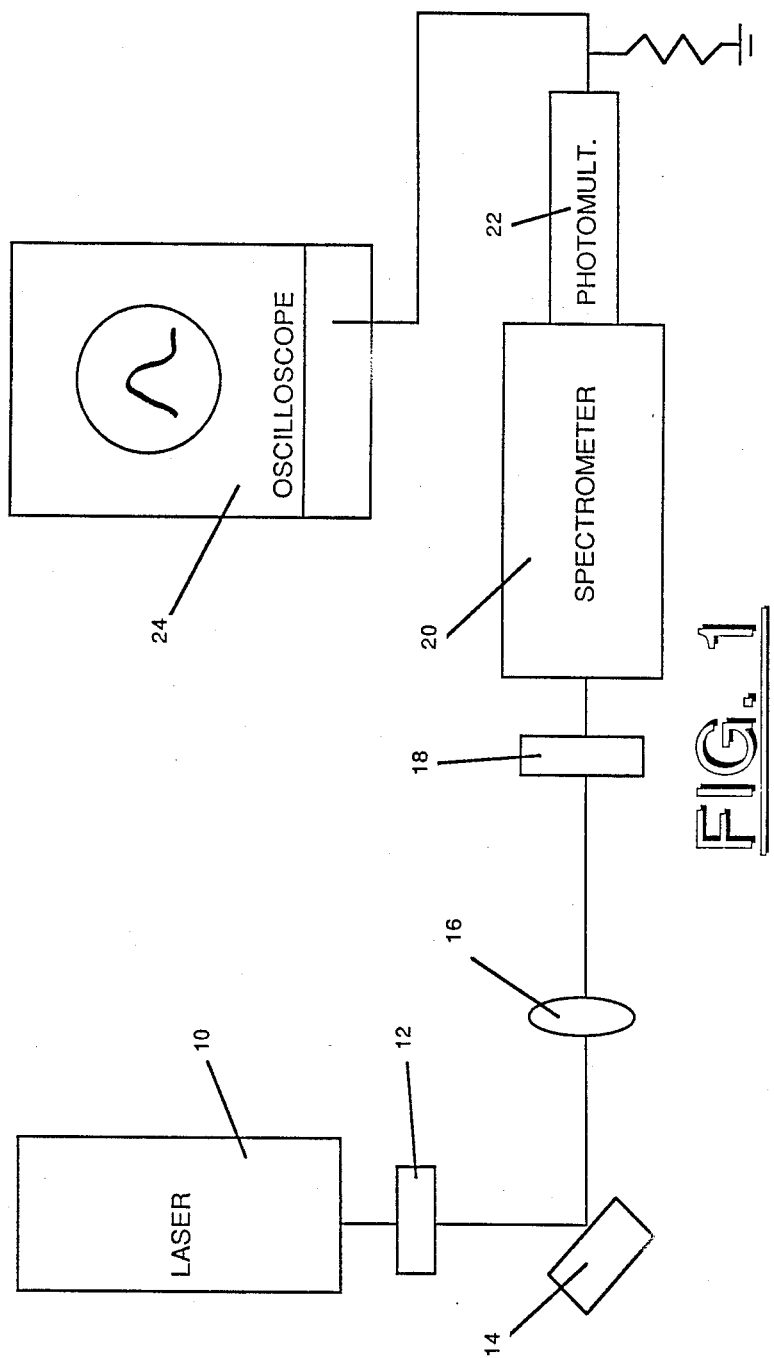
FIG. 1 is a schematic representation of the configuration of the preferred embodiment of the optical inspection system of the present invention for measuring total luminescence of a material as a function of time.
Figure 2:
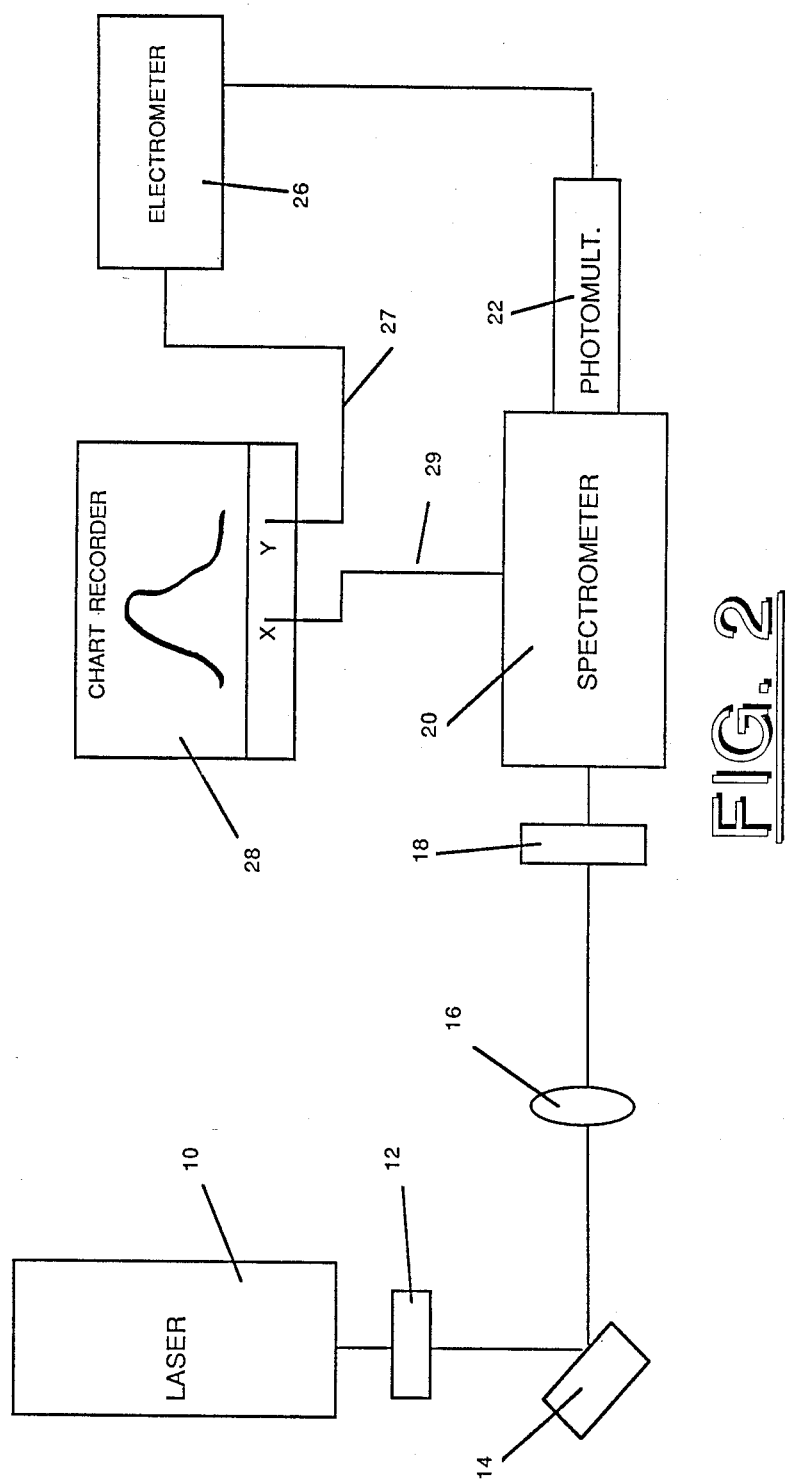
FIG. 2 is a schematic representation of the configuration of the preferred embodiment of the optical inspection system of the present invention for measuring total luminescence of a material as a function of wavelength.
Figure 4:
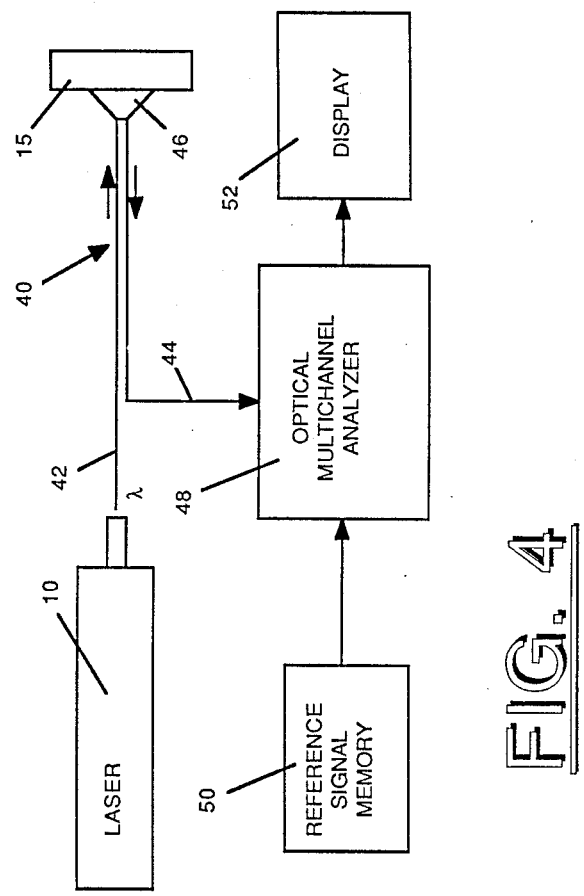
FIG. 4 is a schematic representation of an inspection system utilizing the luminescece detection apparatus of the present invention.

The preferred embodiment of the invention system for analyzing the quality of a polymer material is shown generally in FIGS. 1, 2 and 4. As was discussed above, the invention quality detection system is based on the recognition of subtle differences in the material. Since the invention system is intended to be used with a wide variety of polymer materials, it is necessary to make an initial determination of the fluorescence characterstics of the particular material using the system shown in FIGS. 1 and 2 to establish a reference spectral response for the material. Once the reference fluorescence characteristics of the material have been determined, these characteristics can be stored and correlated with subsequent measurements.

For the initial determination, light from an excitation source 10 is passed through a shutter 12 to illuminate the specimen of material 14. In the preferred embodiment, the excitation source is a laser producing light at a specifically selected wavelength to cause fluorescence, as will be discussed in greater detail below. The shutter 12 of the system shown in FIG. 1 can be eliminated if a pulsed laser is used.

The fluorescence characteristics of the material are determined by analysis of the reradiated light which passes through lens 16, filter 18 and is used as input for the spectrometer 20. The filter 18 can be selected to minimize scattered light from the laser 10. The spectrometer 20 disperses the light which is then detected by the photomultiplier 22 and amplified to provide input for a suitable display device, such as the oscilloscope 24 shown in FIG. 1.

Figure 3:
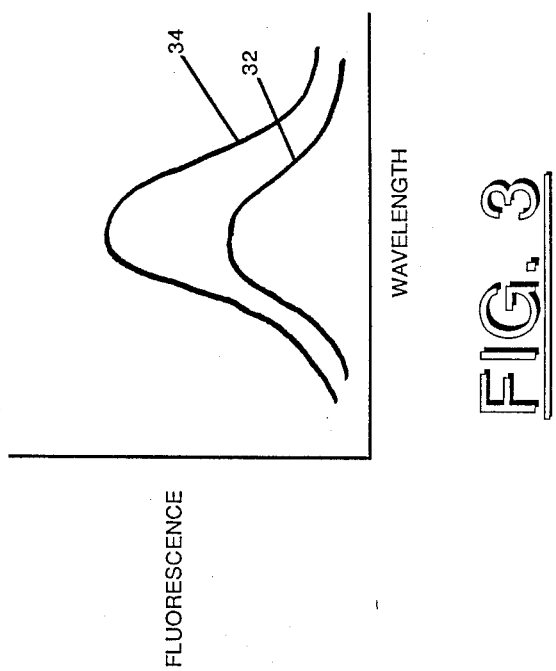
FIG. 3 is a graphical representation of fluorescence amplitude of a material as a function of wavelength.
Figure 6:
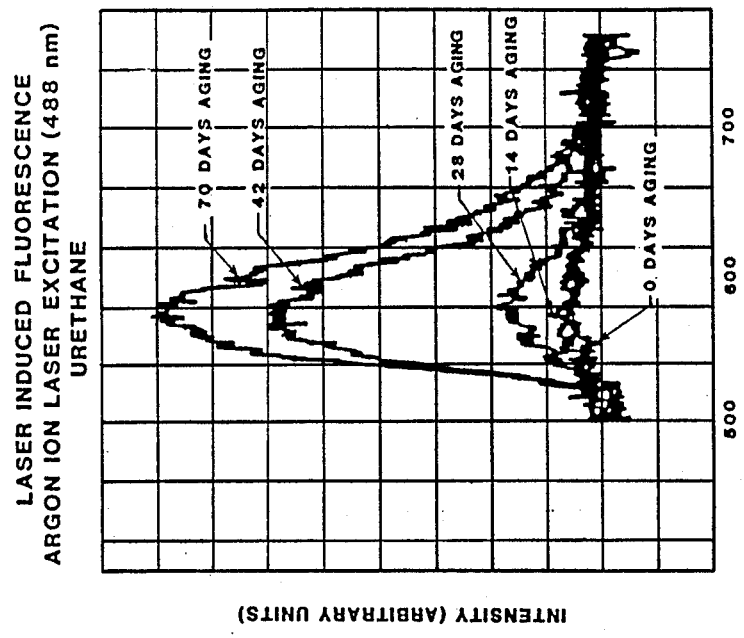
FIG. 6 is a graphical representation of experimental results obtained by using the inspection system of the present invention to compare the fluorescence charactersitics of polyurethane materials having different ages.

The system shown in FIG. 2 for measuring intensity as a function of wavelength comprises many of the elements shown in FIG. 1; however, the output of the photomultiplier is fed to an electrometer 26 which provides a fluorescence amplitude signal, illustrated by line 27, for input into the chart recorder 28. Wavelength information is provided to the chart recorder by line 29. A typical polymer fluorescence output displayed on the chart recorder 28 is shown in FIG. 3. The lower curve 32 represents the spectrum obsrrved for the new polymer material, while the upper curve 34 represents the spectrum of the aged or deteriorated material.

As was mentioned above, the invention system is based on analysis of the fluorescence spectrum of the material to be tested. Laser-induced luminescence is the emission of light resulting from the absorption of laser light by a substance. The wavelength of the reradiated light contains a major portion at the wavelength of the exciting laser light. However, it also contains many new wavelength components which are determined by the molecular structure of the absorbing material. The present invention is based on the discovery that polymer materials, such as polyester-based and polyether-based polyurethanes have distinctive characteristic responses to radiation at certain frequencies. In particular, these characteristic responses can be used to differentiate between various samples of the polymer-based materials to detect deterioration.

For a given excitation spectrum, samples of a material can have different fluorescence or phosphorescence spectra, even though they appear visually similar. The method and apparatus of the present invention differs from standard ultraviolet fluorescence techniques in that it takes advantage of the complicated excitation-luminescence spectra of the polymer material.

One would not normally think of polyurethane as a fluorescent material because, under standard room light conditions, the dominant process is simple light scattering and absorption. The wavelength dependence of these processes gives the polyurethane its characteristic color. Each photon of light is either absorbed or scattered by the polyurethane, but the wavelength remains essentially the same. Since room light contains all visible wavelengths, any fluorescence effects are completely masked. The desired fluorescent effects can be observed, however, by illuminating the polyurethane with laser light at an appropriate wavelength, e.g., 488 nm, and looking at it through a filter that only passes longer wavelengths.

The present invention detects deterioration of polymer-based materials based on a quantitative comparison of the peak fluorescence intensity of a specimen at a particular wavelength with the peak intensity fluorescence of a reference sample of the material at that wavelength. A preferred embodiment of a system for making such a quantitative comparison is shown generally in FIG. 4. The system comprises a laser 10 which produces light at a specific wavelength known to cause fluorescence in the specific polymer being analyzed. The specific wavelength for this excitation can be determined using the systems shown in FIGS. 1 and 2, as discussed hereinabove. The light produced by the laser 10 is transmitted to the specimen 15 by a fiber optic bundle 40 comprising a transmitting fiber 42 and a receiving fiber 44. A shroud 46 is attached to the bundle 40 to shield the tested area from interference by ambient light.

The fluorescence produced by the specimen 15 in response to the laser illumination is transmitted via return fiber 44 to optical analyzing circuitry. The analyzing circuitry for comparing the fluorescene spectrum of the specimen with the fluorescence spectrum of the reference sample can be in a number of different configurations, including either of the configurations shown in FIGS. 1 and 2. In the preferred embodiment, however, the reflected signal is provided to the input port of an optical multichannel analyzer 48. The optical multichannel analyzer is also provided with reference fluorescence data which is stored in an appropriate memory device 50, which data corresponds to the fluorescence characteristics of a polymer material of known quality. This reference data is obtained using either of the system configurations shown in FIGS. 1 or 2. The optical multichannel analyzer 48 compares the data from the specimen 15 to the stored data from the reference sample 14 and provides an output signal which is correlatable with the quality of the specimen. This output is then displayed on an appropriate display device 52

Figure 5:
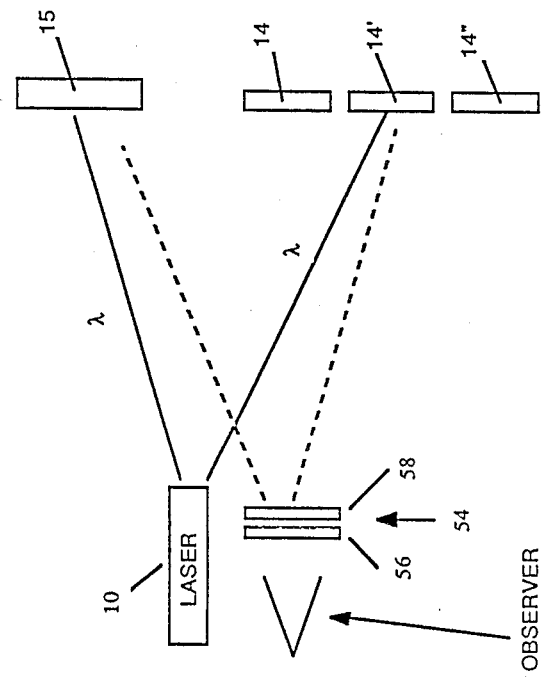
FIG. 5 is an illustration of an alternate embodiment of the present invention for utilizing a visual technique to inspect a polymer material.

An alternate system for obtaining a qualitative indication of the condition of a polymer material is shown generally in FIG. 5. In ths embodiment, the specimen 15 is illuminated with a laser 10 which produces light at an appropriate frequency to cause the polymer material to fluoresce. The operator is provided with a series of reference samples, illustrated generally as 14, 14', and 14", with each of the samples corresponding to a known condition of deterioration of the polymer material. The operator obtains his reference reading by selecting one of the samples, e.g., 14', and illuminating it with light from the laser 10 while viewing it through a filter system 54 comprising an appropriate color filter 56 (e.g., OG 530) and a neutral density filter 58. The value of the neutral density filter 58 is chosen such that the intensity of the flourescence radiation from the reference sample 14' is reduced to the threshold of visibility. The value of the netural density filter 58 which satisfies this criterion thus establishes the "zero" reference point for inspecting the specimen 15 for deterioration. As an alternative to substituting neutral density filters, the desired optical attenuation can be achieved by using a cross-polarization filter.

Once the system has been calibrated by selecting the appropriate neutral density filter 58, as described above, the operator illuminates the specimen 15 with the same laser 10 while viewing the specimen through the filter system 54. If the intensity of the fluoresecent radiation from the specimen 15 exceeds that of the reference sample, then the operator is able to make a simple qualitative determination that the specimen 15 is deteriorated to an unacceptable level. The visual method described above is generally less precise than the quantitative method, but is ideally suited to certain field applications where it is desirable to make a rapid determination of the physical condition of a polymer material.

The method and apparatus of the present invention was verified by conducting an experiment to compare samples of polyurethane using the test set-up shown schematically in FIGS. 1 and 2. In ths experiment, samples of the polyurethane were artificially aged by imersing them in 160° F. water for extended periods of time. A pulsed argon ion laser was used as the excitation source for the experiment. The specific laser used was a TWR Model 71A argon-ion laser having a pulse length of 40 micro seconds, a repetition rate of 60 cycles per second and a peak power of approximately 0.040 watts. The sample under observation was illuminated with the unfocussed output of this laser.

Fluorescent light was collected with a lens which focussed the light into a Bausch and Lomb Model 33-86-77 Monochromator with 0.5 mm slits and a 1.0 micron blazed grating, and subsequently detected with a RCA Model 1P21 photomultiplier tube. Various filters were used to reduce the directly scattered laser light entering the spectrometer, for example, an OG530 Schott filter.

The samples had been artificialy aged in 160° F. hot water for time periods ranging up to 70 days. Quantitative measurements were made on this group of specimens using both an argon ion laser (wavelength =488 nm) and a helium cadmium laser (wavelength =325 nm). In addition, qualitative visual measurements were made using a very low-power pulsed argon-ion laser and filters which pass all wavelengths above 530 nm.

The visual qualitative measurements indicated that there is a strong correlation between the fluorescence activity and the age of the sample for the polyurethane. Furthermore, the quantitative measurements indicate that there is a strong correlation between the spectral response and the age of the specimen. A graphical representation (before correction for system response) of data obtained by the quantitative measurements is shown in FIG. 5.

While the method and apparatus of the present invention has been descirbed in connection with the preferred embodiment, it is not intended to be limited to the specific form set forth herein, but on the contrary, it is intended to cover such modifications, alternatives and equivalents as can reasonably be included within the scope and spirit of the invention as defined by the appended claims.

I claim:

1. A method for detecting the deterioration of a specimen of polymer-based material, comprising the steps of:
    obtaining a reference data signal corresponding the the intensity of fluorescent radiation emitted by a reference sample of said polymer-based material when exposed to light having a particular first wavelength, said reference sample of said polymer material having a known physical condition;
    illuminating said specimen of said polymer material with light having a wavelength corresponding to said particular first wavelength;
    detecting fluorescent radiation produced by said specimen after illumination by said light and producing an second data signal in response thereto; and
    comparing said second data signal to said reference data signal to obtain an indication of the physical condition of said specimen.

2. The method according to claim 1, said light comprising laser light.

3. The method according to claim 2, said laser light having a wavelength of approximately 488 nanometers.

4. The method according to claim 3, said step of comparing said first and second data signals further comprising the step of plotting said reference data signal and said second data signal on a chart recorder and visually comparing the resulting charts of said reference data signal and said second data signals.

5. The method according to claim 3, further comprising the step of comparing said reference data signal and said second data signal in an optical multichannel analyzer.

6. A method for detecting the deterioration of a specimen of polymer-based material, comprising the steps of:
    illuminating a reference sample of said polymer-based material with light, said light having a known wavelength for causing said polymer-based material to produce fluorescent radiation;

viewing said reference sample through an optical filter system to obtain a first visual representation of the fluorescent intensity of said sample, said filter system comprising means for attentuating said fluorescent intensity to the threshold of visibility;

illuminating said specimen of said polymer-based material with said light;

viewing said specimen of said polymer-based material through said optical filter system to obtain a second visual representation of fluorescent intensity; and comparing said second visual representation of said fluorescent intensity to said first visual representation of said fluorescent intensity to determine the physical condition of said specimen of said polymer-based material.

7. The method according to claim 6, said light comprising laser light.

8. The method according to claim 7, said reference sample of polymer material being selected from a group of samples, each said sample of said group corresponding to a known physical condition of said polymer material.

9. The method according to claim 8, said means for attenuating said fluorescent intensity comprising a neutral density filter.

10. The method according to claim 8, said means for attenuating comprising a cross-polarization filter.

11. The method according to claim 10, said laser light having a wavelength of approximately 488 nanometers.

* * * * *